United States Patent [19]

Norton et al.

[11] Patent Number: 5,002,934
[45] Date of Patent: Mar. 26, 1991

[54] AQUEOUS GEL COMPRISING CARRAGEENAN

[75] Inventors: Ian T. Norton, Rushden; Charles R. Brown, Bedford, both of Great Britain

[73] Assignee: Van Den Bergh Foods Co., Division of Conopco, Inc., Lisle, Ill.

[21] Appl. No.: 123,100

[22] Filed: Nov. 20, 1987

[30] Foreign Application Priority Data

Nov. 24, 1986 [GB] United Kingdom ............... 8628068

[51] Int. Cl.[5] .................. A61K 31/00; A61K 7/00; C07G 17/00; C08B 37/00
[52] U.S. Cl. .................................... 514/54; 536/52; 536/114; 514/846; 514/847; 424/49; 424/58; 424/59; 424/61; 424/65
[58] Field of Search ................... 514/54, 846, 847; 536/52, 114; 424/49, 58, 59, 61, 65

[56] References Cited

U.S. PATENT DOCUMENTS

| | | | |
|---|---|---|---|
| 2,864,706 | 12/1958 | Stoloff | 426/271 |
| 3,342,612 | 9/1967 | Foster et al. | 501/117 |
| 3,956,173 | 5/1976 | Towle | 252/316 |
| 3,962,482 | 6/1976 | Comer et al. | 426/575 |
| 4,276,320 | 6/1981 | Moirano | 426/575 |
| 4,307,124 | 12/1981 | Moirano | 426/573 |
| 4,543,250 | 9/1985 | Witt | 514/54 |

FOREIGN PATENT DOCUMENTS

| | | |
|---|---|---|
| 542068 | 2/1985 | Australia . |
| 57-185755 | 7/1982 | Japan . |
| 80/01142 | 6/1980 | World Int. Prop. O. . |
| 84/04039 | 10/1984 | World Int. Prop. O. . |

OTHER PUBLICATIONS

The Merck Index, Tenth Edition, Published by Merck & Co., Inc., Rahway, N.J., USA, 1983, p. 260.
Chem. Abstracts, vol. 99 (1983), Abstract 99:157111d.
Chem. Abstract, vol. 103 (1985), Abstract 103:36401r.
"J. Mol. Biol." (1980), 138, 349–362.
"Faraday Discuss. Chem. Soc." (1974), 57, 230–237.

*Primary Examiner*—Ronald W. Griffin
*Assistant Examiner*—Everett White
*Attorney, Agent, or Firm*—Milton L. Honig

[57] ABSTRACT

The invention pertains to aqueous gels, gel-forming compositions and composites containing the same, comprising carrageenan and a cation of such a type and in such a concentration that the gel has a transition midpoint temperature below 45° C. and a yield stress of at least 0.5 kN/m$^2$ at 5° C. The gels or gel-forming compositions can advantageously be used in food and toiletry products.

15 Claims, 3 Drawing Sheets

AQUEOUS GEL COMPRISING CARRAGEENAN

BACKGROUND OF THE INVENTION

1. Field of the Invention

The present invention relates to an aqueous gel comprising carrageenan, to a gel-forming composition and a dry composition to constitute such aqueous gel, and to a composite containing same.

2. The Related Art

For various applications there is a need for aqueous gels that have a fairly high gel strength and a relatively low melting point. For example, for food-products it is often desirable that the gel melts in the mouth to release the flavour. The gelling agent commonly used to meet these demands is gelatin. With gelatin, aqueous gels can be made that usually have a melting point of about 30°–35° C. Gelatin can be used to prepare very weak gels; but, alternatively, rather firm gels can suitably be obtained with gelatin as well. For example, the gel strength of aqueous gelatin gels, as indicated by the yield stress at 5° C., may range from about 0.1 to above 200 kN/m².

However, the use of gelatin is not without disadvantages. For example, gelatin is a rather expensive gelling agent. The gelatin gel sets rather slowly, which can be undesirable. Furthermore, the use of gelatin in food-products can be undesirable for e.g. Jews and Moslems, because it is prepared from pigskin. Despite these disadvantages, however, a commercially acceptable gelling agent for the preparation of fairly strong low melting aqueous gels, that can be used instead of gelatin, has never been found.

Similarly, for aqueous gel cosmetic and pharmaceutical products intended for topical application to the skin, the mucosae or the teeth, it is also desirable that the gel is firm at room temperature yet softens at or near body temperature to facilitate its cosmetic or pharmaceutical benefit.

Kappa- and iota-carrageenan are commonly used polysaccharide gelling agents. With carrageenan gelling agent compositions as commonly available, fairly firm gels can conveniently be obtained. However, such gels have high melting points, e.g. from about 50° C. to about 70° C. or even higher.

The gel melting point is the temperature at which the gel network structure disappears if the gel is heated slowly.

However, in practice it is difficult to determine this temperature accurately and reliably and it is, therefore, common practice to refer to the closely related transition midpoint temperature Tm, which is determined by means of optical rotation dispersion (ORD). The Tm-value of carrageenan gels commonly lies within the experimental error range of the gel melting temperature. However, the Tm-determination via ORD depends on the transition from the ordered to the disordered state. The ordered state may be a gel, but this need not be so. Aqueous carrageenan systems may also occur in the so-called double helix state. In this state, it is believed, pairs of polymer molecules have formed, presumably in a double helix conformation, which is indicated by the ORD measurement as an ordered state, but macroscopically the system is still a pourable liquid, because no wide ranging three dimensional network has formed. Thus, for carrageenan gels the Tm-value usually does not differ substantially from the gel melting point. However, the fact that the midpoint temperature for the order to disorder transition, Tm, can be determined does not imply that the system at the lower temperature is a gel; the ordered state may also be the non-gelled double-helix state.

Although in practice the Tm-value of a carrageenan gel is often used interchangeably with the temperature at which the gel melts, which is correct for the majority of carrageenan gels, substantial differences between the temperature at which a gel comprising carrageenan melts and the Tm-value of that gel, may occur. If for example, in a carrageenan gel composition that has a Tm-value and a gel melting point of about 50° C., locust bean gum is incorporated, this can cause an increase of the temperature at which the gel melts to e.g. about 55° C. or 60° C. without changing the Tm-value of the order to disorder transition. For the large majority of carrageenan gels, however, the gel melting point does not differ substantially from the Tm-value.

It is well known that the properties of aqueous carrageenan systems may vary substantially in dependence of the type and quantity of ions contained in the system.

In U.S. Pat. No. 2,864,706 it is described that the elasticity of carrageenan gels can be improved by incorporating the potassium salt of a sequestering agent, which serves to chemically bind the ions to which the brittleness of conventional carrageenan gels is attributed and to supply an abundance of potassium to enhance gelation.

U.S. Pat. No. 3,962,482 is directed to clear, elastic, water gels and gel-forming compositions that include a potassium salt and a potassium sensitive carrageenan. The gels and the gel-forming compositions are characterized by essentially complete freedom from polyvalent metal ions.

In U.S. Pat. No. 3,956,173 it is described that kappa-carrageenan becomes readily soluble in cold water when it is converted to the sodium salt form. The solubility is said to be considerably reduced by the presence of potassium salts. U.S. Pat. No. 3,956,173 teaches to encapsulate a potassium salt, such as e.g. potassium chloride, with a water-soluble hydroxypropyl cellulose, and to blend it in dry form with sodium kappa-carrageenan, before addition of the mixture to water to effect gelling.

U.S. Pat. No. 4,307,124 describes the preparation of a carrageenan gel with the use of a composition that is swellable in cold tap water and gels at room temperature. The composition comprises kappa-carrageenan containing less than 5 wt. % of each of potassium and calcium cations, potassium bitartrate, cold soluble locust bean gum and a sodium salt of a sequestering agent. The sequestering agent is present in an amount sufficient to sequester substantially all of the polyvalent cations present when the composition is dissolved in cold tap water.

Although the above mentioned publications are directed to various objectives, they have in common that the disclosed gels have high melting points. The mid point temperature of the order to disorder transition, Tm, is above about 45° or 50° C. and for the majority of the disclosed gel compositions it is substantially higher.

U.S. Pat. No. 4,276,320 discloses gels with relatively low melting points, e.g. at about body temperature. The gel-forming compositions comprise kappa-carrageenan, potassium in an ionizable form in an amount sufficient to provide the sol (after solution of the composition in an aqueous medium) with a potassium ion content of from about 200 to about 800 ppm, and a sodium salt of a sequestering agent in an amount sufficient to sequester substantially all of the polyvalent cations present in the sol. The gels disclosed in U.S. Pat. No. 4,276,320 have Tm-values well below 45° C. However, the gels are extremely weak. At 1° C., the yield stress is below the measurement range of a conventional Instron ® Tester. At refrigerator temperature, the gels do not retain their shape but are still pourable.

SUMMARY OF THE INVENTION

It has now been found that without using gelatin, relatively strong, low melting gels can be made. Such gels can be made using carrageenan as gelling agent.

Sequestering agents need not be used and ordinary tapwater can be employed to prepare the gel.

According to one aspect, the present invention provides an aqueous gel comprising carrageenan which gel contains a cation (A) of a type and in a concentration effective to cause the gel to have a transition midpoint temperature below 45° C., the carrageenan being kappa-carrageenan, iota-carrageenan or a mixture thereof, and having a concentration effective to cause the gel to have a yield stress of at least 0.5 kN/m² at 5° C. Preferably, the cation (A) is selected from the group consisting of potassium, ammonium, calcium, magnesium, aluminum, rubidium and mixtures of two or more thereof. Preferably the gel further contains a cation (B) selected from the group consisting of sodium, lithium, $NH_{4-n}(CH_3)_n$ wherein n=1, 2, 3 or 4, and mixtures of two or more thereof.

BRIEF DESCRIPTION OF THE DRAWING

For a fuller understanding of the invention, reference may be had to the following drawing in which.

DETAILED DESCRIPTION

In this specification by aqueous gel is meant that the liquid with which the gel has been made up is an aqueous liquid, i.e. containing water as solvent.

Throughout this specification by carrageenan is meant gelling carrageenan, i.e. kappa-carrageenan, iota-carrageenan or a mixture thereof. Non-gelling carrageenan such as lambda-carrageenan is explicitly indicated as such.

The characteristics of the present aqueous carrageenan gel are governed by the following properties:

The presence of cation (A) is required to be able to obtain a sufficiently strong gel. For kappa-carrageenan gels, in particular rubidium, aluminum and especially potassium are effective to enhance the gel strength. For iota-carrageenan suitably potassium and magnesium and especially calcium can be employed.

The transition midpoint Tm is determined by the ionic environment of the polymer and is, in principle, independent of the carrageenan concentration itself. At a particular ionic composition, the Tm-value is, generally, different for kappa- and iota-carrageenan. For mixtures of kappa- and iota-carrageenan, the Tm-value varies linearly with the fractions of kappa- and iota-carrageenan in the mixture, between the two extreme Tm-values observed for the pure carrageenan forms in that ionic environment.

The gel strength at a given ionic composition, is determined by the concentration of kappa- and iota-carrageenan.

The incorporation of cation (B) is preferred, inter alia because it reduces the brittleness of the gels, thereby making them more elastic and thus more like gelatin gels. The presence of e.g. sodium chloride can further be beneficial, for example for taste reasons if the gel is to be used as or in a food-product.

When applying these rules it should be appreciated that carrageenan preparations always contain cations. Consequently, changing the kind or amount of carrageenan or replacing, for example, one commercial sample of kappa-carrageenan with another one, will in general cause a change in the ionic composition of the aqueous gel, and thereby, inter alia in the Tm-value of the aqueous gel.

However, the cations contained in a carrageenan sample can be exchanged with other cations using methods known per sé.

The ionic content of carrageenan samples can be analyzed accurately. Consequently, the ionic contribution of the carrageenan to the aqueous gel composition can, to some extent, be chosen freely and can be known accurately.

The Tm-value of the gels is determined by the ionic content. The ionic content to be chosen to obtain an aqueous gel having a pre-determined Tm-value, can be determined in the following manner. A series of kappa-carrageenan gels with various ionic contents is prepared and the Tm-values thereof are measured. Similarly the Tm-values of a series of iota-carrageenan gels with those same ionic contents are measured. The Tm-value of a mixture of kappa- and iota-carrageenan at a given ionic composition is then determined by $$Tm^i (mixture) = X\, Tm^i_{kappa} + (1-X)\, Tm^i_{iota} \qquad (1)$$

wherein X indicates the weight fraction of kappa-carrageenan in the carrageenan mixture, and $Tm^i_{kappa}$, $Tm^i_{iota}$ and $Tm^i$ indicate the Tm-values in ionic environment i for kappa-carrageenan, iota-carrageenan and the carrageenan mixture, respectively. Subsequently, Tm-values for kappa-carrageenan, iota-carrageenan and carrageenan mixtures for intermediate ionic compositions can be calculated from the obtained data using conventional interpolation techniques. In this manner, the Tm-value for a specific ionic composition at a given ratio of kappa- and iota-carrageenan can be predicted.

A suitable way to carry out such an analysis of the experimental data, is to derive expressions by which the concentrations of the various cations can be converted into equivalent concentrations of one particular cation. The ionic content of a composition can thus be characterized by a total equivalent concentration of one cation. An equation for the Tm-value can subsequently be derived, expressed as a function of that total equivalent cation concentration.

For example, it was found that for kappa-carrageenan the sodium concentration [Na+] can be expressed as an equivalent potassium concentration $[K^+]^{Na}_{eq}$ by means of the following equation:

$$\ln[K^+]^{Na}_{eq} = 1.12 \ln[Na^+] - 3.31 \qquad (2)$$

The Tm-value for kappa-carrageenan, in °C., can be estimated from:

$$Tm = 1/(-1.61 \cdot 10^{-4} \ln[K^+]^{tot}_{eq} + 2.614 \cdot 10^{-3}) - 273 \qquad (3)$$

If only Na+ and K+ are present, then $[K^+]^{tot}_{eq}$ equals the sum of the K+-concentration and the equivalent K+-concentration calculated with equation (2) for the Na+-concentration:

$$[K^+]^{tot}_{eq} = [K^+] + [K^+]^{Na}_{eq}$$

If, apart from Na+ and K+, other cations are present also, their influence can be taken into account in a similar manner as done for sodium.

For iota-carrageenan the expressions corresponding to equations (2) and (3) are:

$$\ln[K^+]^{Na}_{eq} = 1.26 \ln[Na^+] - 0.53 \qquad (4)$$

$$Tm = 1/(-1.71 \cdot 10^{-4} \ln[K^+]^{tot}_{eq} + 2.775 \cdot 10^{-3}) - 273 \qquad (5)$$

For mixtures of kappa- and iota-carrageenan an estimation of the Tm-value for a given ionic environment can then be obtained with expression (1) by inserting the Tm-values calculated with equations (3) and (5).

Figure 1:
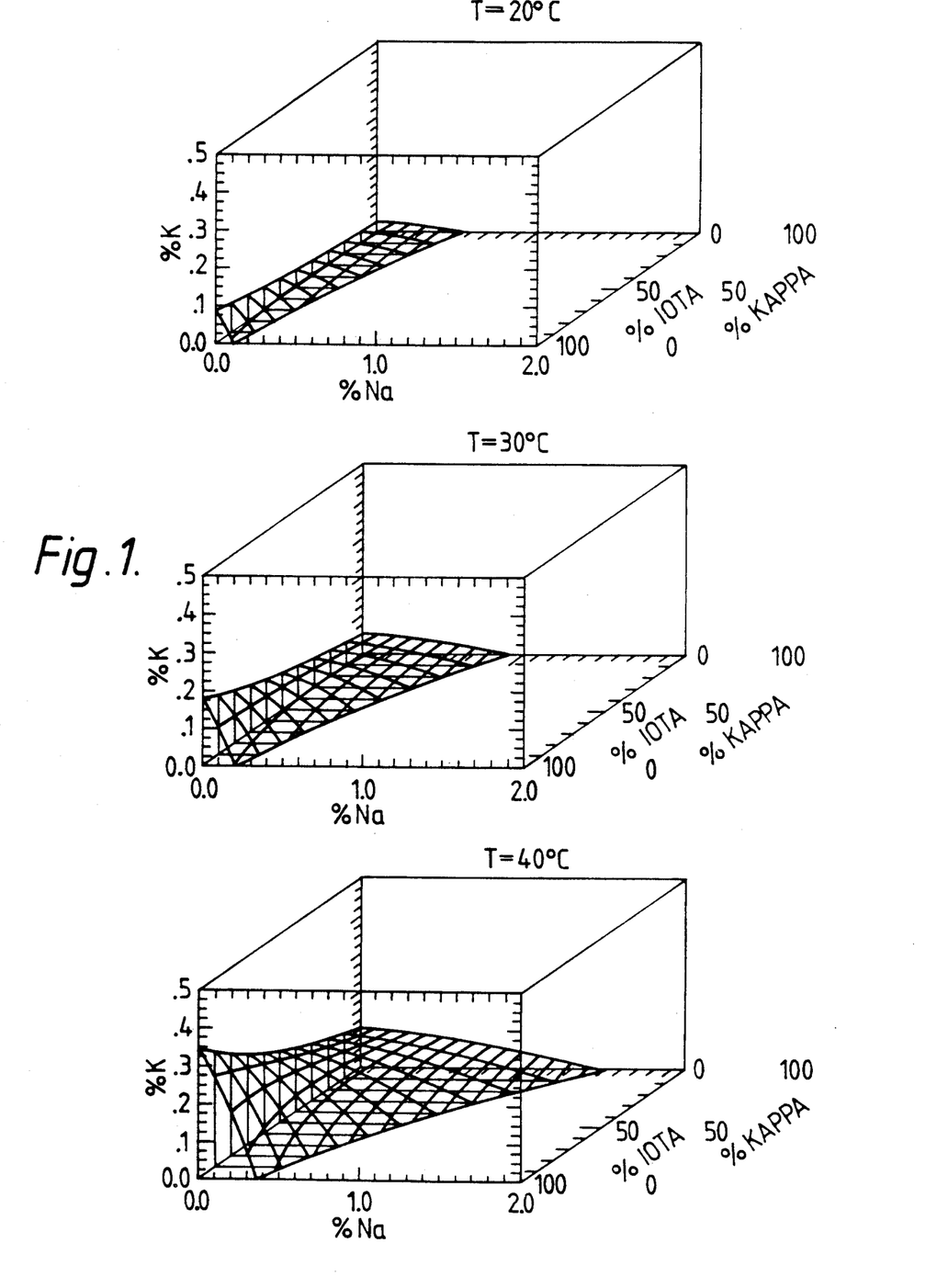
FIG. 1 illustrates the relationship between the Tm-value at three different temperatures relative to the fractions of kappa- and iota-carrageenan in the composition where only potassium and sodium salts are present.

Additionally, using the same experimental data, by means of mathematical methods known per sé, it can be calculated with which ionic composition, in dependence of the relative amounts of kappa and iota-carrageenan, a predetermined Tm-value can be obtained. This is illustrated in FIG. 1. The three plots show, how a Tm-value of 20°, 30° or 40° C. can be obtained, dependent on the fractions of kappa- and iota-carrageenan in the carrageenan composition, if the only salts to be present are potassium and sodium salts.

Figure 2:
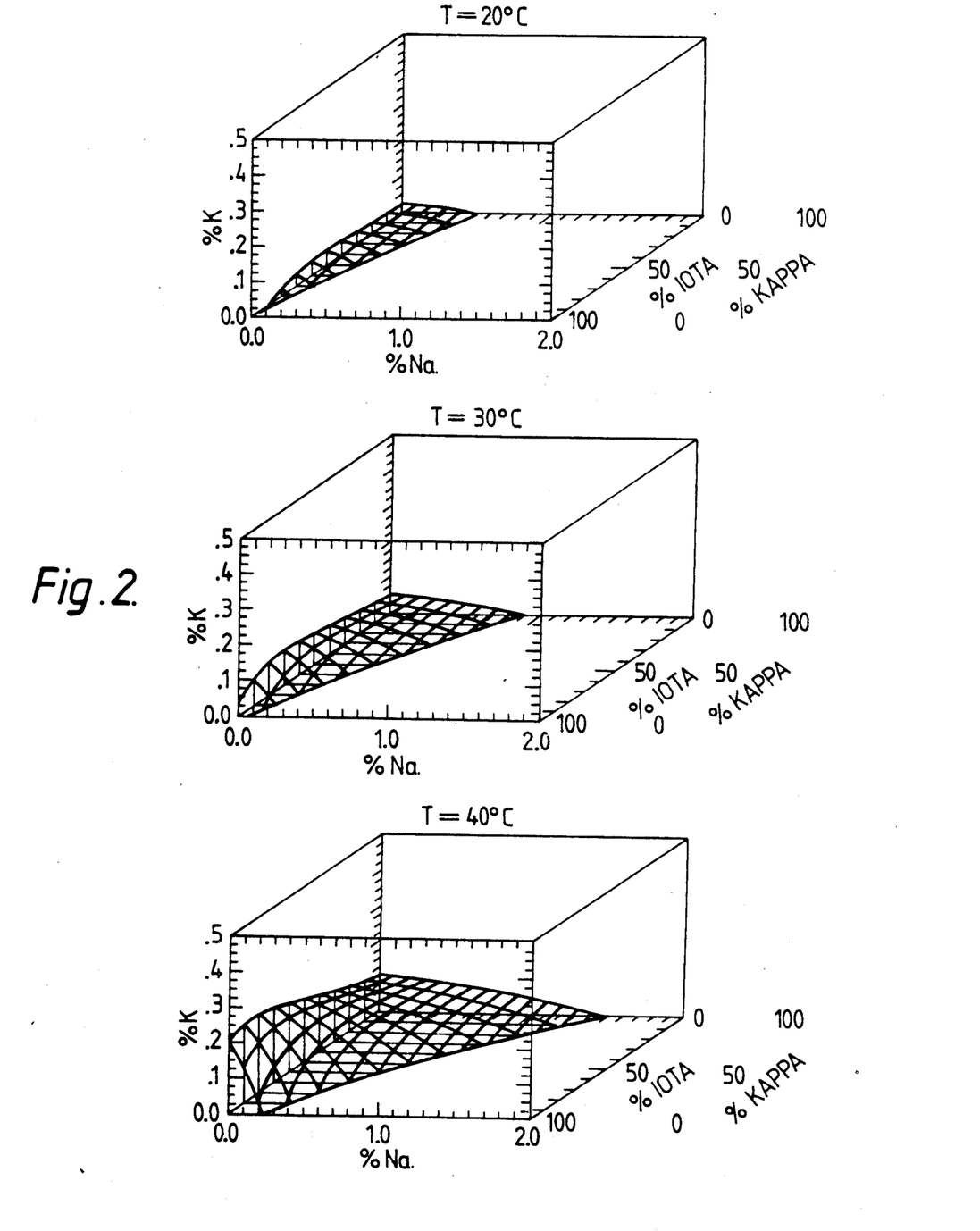
FIG. 2 illustrates a relationship similar to that of FIG. 1 except that the gel compositions are formed using tapwater containing certain levels of calcium, magnesium, sodium and potassium ions instead of deionized water.

These plots can only be used to obtain a pre-selected Tm-value if essentially no other cations than potassium and sodium will be included in the aqueous gel, which implies that the carrageenan samples to be used are in the sodium or the potassium form and that the water used to make up the gel composition is deionized or distilled water. However, the ionic contributions of the carrageenan sample or the tapwater if that is to be used, can be taken into account in a straightforward manner. For example, in FIG. 2, three plots are shown, corresponding to those of FIG. 1, for the case that the gel compositions are to be made up using tapwater containing 133 ppm $Ca^{2+}$, 6 ppm $Mg^{2+}$, 37 ppm Na+ and 6 ppm K+ instead of with water containing no ions.

In a similar manner the gel strength of particular compositions can be predicted. Alternatively, it can be calculated with which compositions a preselected gel strength can be obtained. In practice, however, the precise strength of the gel is usually not a critical parameter, and it is commonly sufficient to measure the gel strength of only a limited number of compositions and to choose an appropriate carrageenan concentration at a suitable ionic composition on the basis of such a limited set of data.

To illustrate of the above, the following procedure can be used to design a moderately strong carrageenan gel having a Tm-value of about 30° C. and containing for taste reasons about 0.5 wt. % NaCl and to ensure microbiological stability 0.05 wt. % potassium sorbate. The available gelling agents are iota-carrageenan containing 6.30 wt. % Na+ and 1.60 wt. % K+ and kappa-carrageenan containing 4.82 wt. % Na+ and 2.48 wt. % K+. Deionized water is to be used to make up the gel.

One of the ways to approach this problem is to estimate first how much carrageenan can be used while keeping the Tm-value below about 30° C. Increasing the carrageenan content causes an increase of the Na+ and K+ concentrations and thereby of the Tm-value. The Tm-values, estimated using equations 1-5, for compositions containing, apart from 0.5 wt. % NaCl ([Na+]=0.086 M) and 0.05 wt. % potassium sorbate ([K+]=3.33 mM), varying amounts of either the kappa-carrageenan or the iota-carrageenan or a 1:1 weight mixture of the two, are shown in Table 1.

The table shows that when using more than 1.5 wt. % carrageenan, whether kappa-, iota- or the 1:1 mixture, the Tm-value will become too high.

TABLE 1

| carrageenan polymer (wt. %) | [Na+] (M) | [K+] (mM) | Total cation [Na+] (M) | [K+] (mM) | Tm (°C.) kappa | iota | mixture |
|---|---|---|---|---|---|---|---|
| kappa | | | | | | | |
| 0.50 | 0.010 | 3.17 | 0.096 | 6.50 | 23.8 | | |
| 0.75 | 0.016 | 4.75 | 0.102 | 8.08 | 26.3 | | |
| 1.00 | 0 021 | 6.34 | 0.106 | 9.67 | 28.4 | | |
| 1.25 | 0.026 | 7.93 | 0.112 | 11.26 | 30.3 | | |
| 1.50 | 0.031 | 9.51 | 0.116 | 12.84 | 32.0 | | |
| 1.75 | 0.037 | 11.10 | 0.122 | 14.43 | 33.6 | | |
| iota | | | | | | | |
| 0.50 | 0.014 | 2.05 | 0.100 | 5.38 | | 26.8 | |
| 0.75 | 0.020 | 3.07 | 0.106 | 6.40 | | 28.2 | |
| 1.00 | 0.027 | 4.09 | 0.113 | 7.42 | | 29.6 | |
| 1.25 | 0.034 | 5.12 | 0.120 | 8.45 | | 31.0 | |
| 1.50 | 0.041 | 6.14 | 0.126 | 9.47 | | 32.1 | |
| 1.75 | 0.048 | 7.16 | 0.133 | 10.49 | | 33.3 | |
| kappa/iota 1:1 (wt) mixture | | | | | | | |
| 0.50 | | | 0.098 | 5.94 | 23.0 | 26.7 | 24.9 |
| 0.75 | | | 0.104 | 7.24 | 25.2 | 28.2 | 26.7 |
| 1.00 | | | 0.110 | 8.54 | 27.2 | 29.6 | 28.4 |

TABLE 1-continued

| carrageenan polymer (wt. %) | [Na+] (M) | [K+] (mM) | Total cation [Na+] (M) | [K+] (mM) | Tm (°C.) kappa | iota | mixture |
|---|---|---|---|---|---|---|---|
| 1.25 | | | 0.116 | 9.86 | 29.0 | 30.9 | 29.9 |
| 1.50 | | | 0.121 | 11.16 | 30.5 | 31.9 | 31.2 |
| 1.75 | | | 0.127 | 12.46 | 32.0 | 33.1 | 32.6 |

When using, for example, the kappa-carrageenan in an amount of about 1-1.5 wt. %, in the presence of 0.5 wt. % NaCl and 0.05 wt. % potassium sorbate a Tm-value of 30°±2° C. will be obtained. If it is desirable to use less than 1% kappa-carrageenan, a Tm-value of about 30° C. can be obtained by adding additional salt, e.g. some KCl. The influence of various, additional amounts of KCl on the Tm-values can be calculated in a similar way by using equations 2 and 3. When employing the 1:1 mixture, a Tm-value of about 30° C. will also be obtained without adding extra cations, when using about 1-1.5 wt. % carrageenan polymer.

Selection of a carrageenan combination to give the desired gel strength can be made by reference to a table of gel strengths obtained from a small series of tests. (For example, comparison of table 1, with the table of Example 1 shows that about 1.5 wt. % of the 1:1 kappa/iota carrageenan mixture is likely to be appropriate to obtain a moderately strong gel with a Tm-value of about 30° C., in the presence of 0.5 wt. % NaCl and 0.05 wt. % potassium sorbate.)

Should it turn out that with the maximum polymer concentration that can be allowed to obtain a desired Tm-value, a sufficiently strong gel cannot be obtained, then one should try using carrageenan samples with different cation contents.

The anions contained in the salts with cations (A) and (B) are not critical. Suitably the anion of the salts is the carrageenan polymer, chloride, sulphate or a mixture thereof. Other anions, e.g. fluoride and/or nitrate, can however also be present. Suitably the salts employed are soluble in water.

The aqueous gel may comprise additional ingredients, e.g. colouring matter and taste and flavour or fragrance compounds dependent upon the intended end use of the gel, provided that such additional ingredients do not adversely affect the gel properties. If, for example, that is considered desirable, some gelatin may also be incorporated in the aqueous gel without adverse effects. Similarly, the gel may contain non-gelling thickening agent, provided it does not raise the Tm-value to above 45° C. or reduce the yield stress to below 0.5 kN/m². For example, the gel may contain a non-gelling thickening agent like lambda-carrageenan.

Preferably, the Tm-value of the gel is 10°-40° C., more preferably it is 20°-35° C. The gel preferably has a yield stress of 1-100 kN/m²; more preferably the yield stress is 10-50 kN/m².

The concentration of kappa- and iota-carrageenan determines, at a given ionic composition, the strength of the gel. Conversely, the content of carrageenan that can suitably be applied varies with the ionic environment of the polymer. Usually, however, a total carrageenan content of 0.3-10 parts by weight per 100 parts by weight of water, is adequate; a total carrageenan content of 0.5-5 parts by weight, in particular of 1-4 parts by weight, per 100 parts by weight of water being preferred.

The above amounts of carrageenan are based on the water being effectively fully available to form the gel network structure. Less amounts of carrageenan, as low as 0.1 part by weight per 100 parts by weight of water, may be sufficient to obtain a gel network structure, if the effective water content of the carrageenan-containing aqueous phase composition is reduced e.g. by incorporating part of the water "phase-separated" from the carrageenan-containing water. This may be the case where the gel according to the present invention is part of a multi-phase system, such as e.g. a water-in-oil emulsion, where part of the water is included as a dispersed non-gel-forming aqueous phase, and the remainder of the water is contained in a carrageenan-containing gel-forming composition according to the present invention dispersed in the continuous fat phase separate from the first non-gel-forming aqueous phase. As a consequence, in such systems the effective carrageenan concentration can be sufficiently high to cause formation of the gel network structure, even though the carrageenan content expressed in relation to the total amount of water would seem to be too low to obtain gelation.

Figure 3:
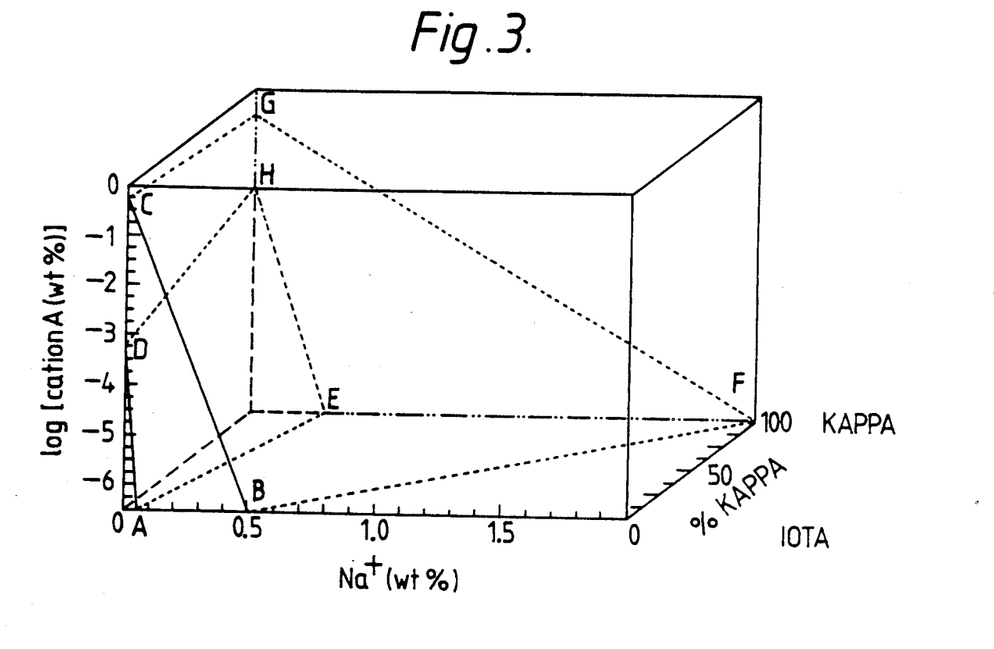
FIG. 3 illustrates the concentration relationships between cations (A) and (B) relative to the weight ratio of kappa- and iota-carrageenan present in the gel composition.

As described hereinbefore, the optimal amounts of cations (A) and (B) to be present in the gel depends on the desired gel strength and transition midpoint temperature as well as on the precise choice of the cations (A) and (B). In practice, however, it is preferred that the gel comprises cations (A) and (B), in dependence of the weight ratio of kappa- and iota-carrageenan present in the gel, in concentrations within the ranges corresponding to space ABCDEFGH of FIG. 3.

Figure 4:
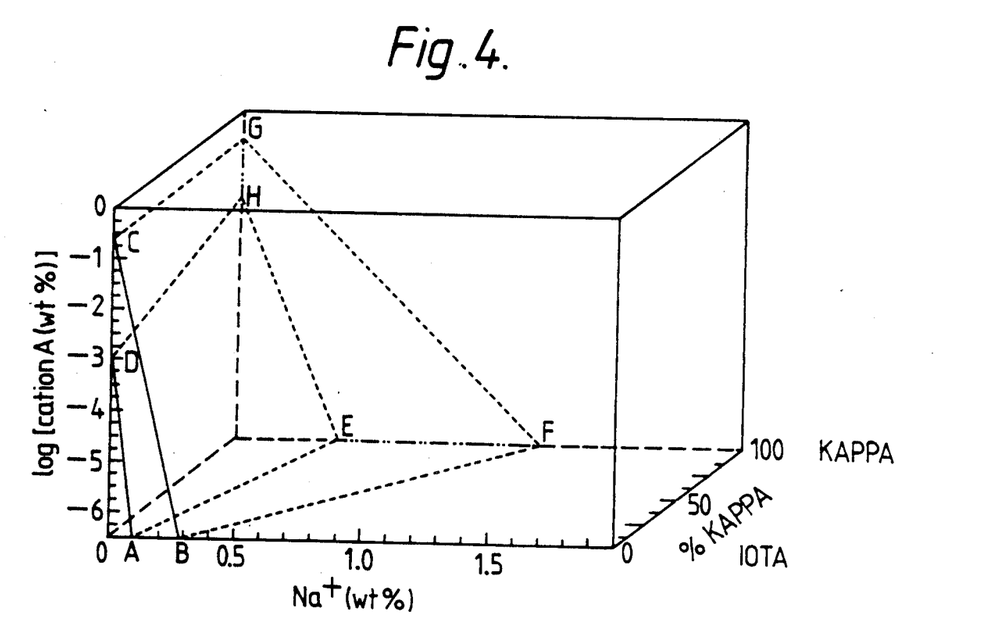
FIG. 4 illustrates a relationship similar to that of FIG. 3 except that preferred concentration ranges are outlined therein.

More preferred ranges for the concentrations of cations (A) and (B) to be present in the gel, correspond to space ABCDEFGH of FIG. 4.

The gel preferably contains 0.5-5 parts by weight of carrageenan per 100 parts by weight of water. When the carrageenan employed comprises from 50-100 wt. % kappa-carrageenan and 0-50 wt. % iota-carrageenan then it is preferred for the gel to contain 0.01-0.25 wt. % K+, 0.1-2 wt. % Na+ and/or 0.04-3 wt. % $Ca^{2+}$. If, alternatively, the carrageenan consists of 50-100 wt. % iota-carrageenan and 0-50 wt. % kappa-carrageenan then preferably the gel comprises 0.01-0.6 wt. % $Ca^{2+}$, 0.01-0.7 wt. % $Mg^{2+}$, 0.05-0.5 wt. % K+ and/or 0.05-1 wt. % Na+.

The gel structure of the aqueous gels described hereinbefore disappears if the temperature is raised to above the gel melting point. Similarly, no gel network is formed if the ingredients are mixed together at a temperature above the gel melting point, or if the temperature is raised to above the melting point before the gel has set. It is to be understood that the present invention encompasses a gel-forming composition containing carrageenan, that constitutes an aqueous gel as hereinbefore described, when kept at a temperature of 5° C.

According to yet another aspect, the present invention provides a dry composition containing carrageenan, that constitutes an aqueous gel as hereinbefore described, when solubilized in an adequate amount of water and subsequently kept at 5° C.

The present aqueous gels, gel-forming compositions and dry compositions suitable for the preparation thereof, can beneficially be used for the preparation of a variety of products. Accordingly, in yet another aspect of the present invention there is provided a composite containing an aqueous gel, a gel-forming composition or a composition suitable for the preparation thereof, as hereinbefore described. Preferred composites are food products and toiletries.

Examples of food products i.e. products intended for human or animal consumption, that can beneficially be prepared with the use of the present invention are meat products, such as paté's, sausages and canned ham in jelly, sauces, soups, in particular dry soups, such as low-calorie instant soups, confectionery gels and yoghurt-type products.

One major advantage of the carrageenan gels of the invention is that they have desirable rheological properties as personal care products. Their melting characteristics also make them suitable vehicles for the incorporation and delivery of other ingredients which are intended to provide enhanced benefits. For example, moisturising, conditioning, cleansing and UV-absorbing agents can be added to skin, nail and hair care formulations. For dental care, agents can be incorporated to help clean teeth and prevent caries, plaque, tartar and gum disease. Colouring agents, preservatives and fragrances, and other ingredients conventionally employed in the manufacture of personal care products intended for topical application to the skin, mucosae and the teeth can also be incorporated in the aqueous carrageenan gels according to the invention.

Examples of toiletry products for which the present invention can advantageously be employed include, but are not restricted to, skin and dentifrice creams or gels and shampoos. A particular advantage of skin care products containing the carrageenan gel according to the invention is their ability to match the sensory properties of conventional emulsions without the presence of any oil whatsoever. It is also possible to incorporate the aqueous gels of the invention in oil-in-water or water-in-oil emulsions without loss of the melting characteristics of the gel, provided that the amount of oil present in the emulsion does not exceed 10% by weight.

In the following examples the yield stress is determined by measuring the force at break at 5° C., using the procedure as described in J. Mol. Biol. (1980) 138, 349–362, and dividing the measured force by the cross sectional area (i.e. $1.13 \cdot 10^{-4} m^2$). The midpoint temperature (Tm) of the transition from the ordered to the disordered state is determined by means of optical rotation measurement as described in Faraday Discuss. Chem. Soc. (1974), 57, 230–237.

EXAMPLE 1

A series of gels was made with varying amounts of kappa- and/or iota-carrageenan and of added NaCl and KCl. The carrageenan and the salts were dissolved in water at 60° C. The mixture was then cooled down to refrigerator temperature, and the gel was allowed to set. The kappa-carrageenan employed contained 4.82 wt. % $Na^+$ and 2.48 wt. % $K^+$. The iota-carrageenan contained 6.30 wt. % $Na^+$ and 1.60 wt. % $K^+$. The transition midpoint temperature, the yield stress and, as indication for the elasticity, the deformation at rupture was determined for each of the gels. The results are given in table 2.

TABLE 2

| carrageenan | | Added salt | | Total cation | | | | Gel properties | | |
|---|---|---|---|---|---|---|---|---|---|---|
| polymer (wt. %) | wt. fraction kappa | NaCl (wt. %) | KCl (wt. %) | $Na^+$ (wt. %) | (M) | $K^+$ (wt. %) | (mM) | Tm (°C.) | Yield stress ($kN/m^2$) | Deformation at rupture (%) |
| 1.5 | 0.50 | 0.8 | 0.03 | 0.39 | 0.17 | 0.023 | 5.9 | 32 | 12 | 67 |
| 1.5 | 0.50 | 0.5 | 0.07 | 0.28 | 0.12 | 0.036 | 9.2 | 30 | 23 | 65 |
| 1.5 | 0.50 | 0.33 | 0.18 | 0.21 | 0.09 | 0.065 | 16.6 | 32 | 32 | 60 |
| 1.5 | 0.25 | 0.75 | 0.05 | 0.38 | 0.17 | 0.027 | 7.0 | 34 | 12 | 74 |
| 1.5 | 0.75 | 0.5 | 0.06 | 0.28 | 0.12 | 0.034 | 8.7 | 28 | 14 | 63 |
| 1.5 | 0.75 | — | 0.16 | 0.08 | 0.03 | 0.060 | 15.4 | 29 | 6.3 | 63 |
| 1.5 | 1 | — | 0.16 | 0.07 | 0.03 | 0.064 | 16.2 | 33 | 0.8 | 42 |
| 1.0 | 1 | 2 | 0.04 | 0.83 | 0.36 | 0.025 | 6.3 | 34 | 1.4 | 81 |
| 2.0 | 1 | 1 | 0.09 | 0.49 | 0.21 | 0.050 | 12.7 | 35 | 38 | 55 |
| 4.0 | 0 | — | 0.11 | 0.25 | 0.11 | 0.064 | 16.4 | 32 | 35 | 85 |

EXAMPLE 2

An acid water dessert gel was made using the following ingredients:

5.36 g kappa-carrageenan (2.48 wt. % $K^+$, 4.82 wt. % $Na^+$)

1.79 g iota-carrageenan (1.60 wt. % $K^+$, 6.30 wt. % $Na^+$)

0.50 g potassium sorbate 0.96 g citric acid 90.2 g sucrose.

The carrageenans were blended and dissolved in 300 g water at 60° C. The sucrose, potassium sorbate and citric acid were dissolved in 200 g water, also at 60° C. The two solutions were mixed together, then poured into moulds and cooled down to 10° C. The gelling temperature was 23° C. A suitable acid water dessert gel was obtained.

The gel had a Tm-value of 34° C. The yield stress measured at 5° C., was 12 $kN/m^2$ and the deformation at rupture was 74%.

The application of the invention to personal care products is further illustrated by the following examples.

EXAMPLE 3

This example illustrates a clear gel which can be used to give the skin a silky smooth feel. It has the following formulation:

| | % (w/w) |
|---|---|
| carrageenan (kappa:iota = 70:30) | 1.0 |
| sodium chloride | 1.0 |
| methylparaben | 0.2 |
| perfume | q.s. |
| water | bal |

This gel had a Tm-value of 30° C., and was prepared as described hereinbefore. The kappa- and iota-carrageenan had the same ion contents as described in example 2. Methylparaben was dissolved prior to dispersing the carrageenan, and perfume was added after the gel had cooled to around 30° C.

EXAMPLE 4

This example illustrates a skin moisturising gel with a rich texture. It has the following composition:

|  | % (w/w) |
| --- | --- |
| kappa-carrageenan | 1.03 |
| iota-carrageenen | 0.44 |
| sodium chloride | 0.59 |
| methylparaben | 0.20 |
| glycerol | 1.0 |
| perfume | q.s |
| water | bal |

This gel had a Tm-value of 41° C. It was prepared by the method described in Example 3, the addition of glycerol being made to the hot carrageenan/salt solution.

EXAMPLE 5

This example illustrates an all-purpose, mild skin cleanser gel, with the following formulation:

|  | % (w/w) |
| --- | --- |
| kappa-carrageenan | 1.03 |
| iota-carrageenan | 0.44 |
| sodium chloride | 0.59 |
| methylparaben | 0.20 |
| ceteth 20 | 7.5 |
| perfume | q.s. |
| water | bal |

This gel had a Tm-value of 41° C. and was prepared by the method described in Example 4.

EXAMPLE 6

This example illustrates a gentle dentifrice with mild abrasive action and protection against caries from monofluorophosphate. It has the following composition:

|  | % (w/w) |
| --- | --- |
| iota-carrageenan (1.60 wt. % K+, 4.82 wt. % Na+) | 1.0 |
| sodium chloride | 0.64 |
| sodium monofluorophosphate | 1.28 |
| ground grape pips | 50 |
| potassium sorbate | 0.05 |
| flavour | q.s. |
| water | bal |

This gel had a Tm-value of 35° C.

EXAMPLE 7

This example illustrates a low-calorie instant soup composition suitable for the preparation of one cup of soup (about 200 ml):

|  | grams |
| --- | --- |
| iota-carrageenan (1.60 wt. % K+, 4.82 wt. % Na+) | 0.6 |
| flavour base (0.48 wt. % K+, 12.1 wt. % Na+) (the flavour base comprising vegetable fat, meat flavours & hydrolysates, vegetable flavours, spices & flavour enhancers) | 8.2 |

This formulation fully dissolved on addition of about 190 ml of hot tap water (over 80° C.). Subsequently, the mixture was allowed to cool down to below 45° C. No gelling occurred at temperatures of over 45° C.

We claim:

1. Aqueous gel comprising carrageenan, which gel contains a cation (A) selected from the group consisting of potassium, ammonium, calcium, magnesium, aluminum, rubidium and cation mixtures thereof and in a concentration effective to cause the gel to have a transition mid-point temperature in the range of 20° to 35° C., the carrageenan being selected from the group consisting of kappa-carrageenan, iota-carrageenan and a mixture thereof, and having a concentration effective to cause the gel to have a yield stress of at least 0.5 kN/m² at 5° C., and the gel not containing any sequestering agents.

2. Aqueous gel according to claim 1, which gel further contains a cation (B) selected from the group consisting of sodium, lithium, $NH_{4-n}(CH_3)_n$ wherein n=1, 2, 3 or 4, and mixtures thereof.

3. Aqueous gel according to claim 2, which comprises cation (A) and (B), dependent upon a weight ratio of kappa- and iota-carrageenan present in the gel, in concentrations within the ranges corresponding to space ABCDEFGH of FIG. 3.

4. Aqueous gel according to claim 3, which comprises cations (A) and (B), in dependence of the weight ratio of kappa- and iota-carrageenan present in the gel, in concentrations within the ranges corresponding to space ABSDEFGH of FIG. 4.

5. Aqueous gel according to claim 1, wherein the yield stress is 1-100 kN/m².

6. Aqueous gel according to claim 5, wherein the yield stress is 10-50 kN/m².

7. Aqueous gel according to claim 1, which comprises 0.3-10 parts by weight of carrageenan per 100 parts by weight of water.

8. Aqueous gel according to claim 7, which comprises 0.5-5 parts by weight of carrageenan per 100 parts by weight of water.

9. Aqueous gel according to claim 1, comprising 0.5-5 parts by weight of a carrageenan per 100 parts by weight of water, the carrageenan consisting of 50-100 wt. % kappa-carrageenan and 0-50 wt. % iota-carrageenan, and containing cations selected from the group consisting of 0.01-0.25 wt. % potassium, 0.1-2 wt. % sodium, 0.04-3 wt. % calcium and mixtures thereof.

10. Aqueous gel according to claim 1, comprising 0.5-5 parts by weight of carrageenan per 100 parts by weight of water, the carrageenan consisting of 50-100 wt. % iota-carrageenan and 0-50 wt. % kappa-carrageenan and containing cations selected from the group consisting of 0.01-0.7 wt. % magnesium, 0.05-0.5 wt. % potassium, 0.05-1% wt. % sodium and mixtures thereof.

11. Dry composition containing carrageenan, that constitutes an aqueous gel according to claim 1 when solubilized in an adequate amount of water and subsequently kept at 5° C.

12. Composite comprising an aqueous gel according to claim 1 and an additional component selected from the group consisting of a flavour, fragrance, colouring agent, preservative and mixtures thereof.

13. Composite according to claim 12 wherein said additional component is a food product ingredient selected from the group consisting of a colouring agent, preservative, flavour and mixtures thereof.

14. Composite according to claim 12 wherein said additional component is a toiletry product ingredient selected from the group consisting of a colouring agent, preservative, fragrance, moisturizing agent, conditioning agent, cleansing agent, UV-absorbing agent, anti-caries agent, anti-tartar agent and mixtures thereof.

15. Composite according to claim 12 wherein said additional component is a skin care product ingredient selected from the group consisting of a colouring agent, preservative, fragrance, moisturizing agent, conditioning agent, cleansing agent, UV-absorbing agent and mixtures thereof.

* * * * *